US005936127A

United States Patent [19]
Zhang

[11] Patent Number: 5,936,127
[45] Date of Patent: Aug. 10, 1999

[54] ASYMMETRIC SYNTHESIS AND CATALYSIS WITH CHIRAL HETEROCYCLIC COMPOUNDS

[75] Inventor: Xumu Zhang, State College, Pa.

[73] Assignee: The Penn State Research Foundation, University Park, Pa.

[21] Appl. No.: 09/006,178

[22] Filed: Jan. 13, 1998

Related U.S. Application Data

[60] Provisional application No. 60/035,187, Jan. 13, 1997, and provisional application No. 60/046,117, May 9, 1997.
[51] Int. Cl.$^6$ .......................... C07F 9/02; C07D 333/50; C07D 209/56; B01J 31/00
[52] U.S. Cl. .............................. 568/12; 549/41; 549/43; 548/418; 548/427; 548/452; 502/162; 502/168
[58] Field of Search ................................. 568/12; 549/41, 549/43; 548/418, 427, 452; 502/162, 168

[56] References Cited

U.S. PATENT DOCUMENTS

| | | |
|---|---|---|
| 3,105,096 | 9/1963 | Welcher . |
| 5,008,457 | 4/1991 | Burk . |
| 5,177,230 | 1/1993 | Burk . |
| 5,258,553 | 11/1993 | Burk . |
| 5,426,223 | 6/1995 | Burk . |
| 5,516,944 | 5/1996 | Broger et al. .............................. 568/13 |
| 5,596,114 | 1/1997 | Burk . |
| 5,723,642 | 3/1998 | Sturmer et al. ............................ 556/18 |
| 5,741,931 | 4/1998 | Naumann et al. .......................... 568/9 |
| 5,783,738 | 7/1998 | Mathey et al. ............................. 568/12 |
| 5,817,848 | 10/1998 | Kamer et al. ............................. 556/12 |

FOREIGN PATENT DOCUMENTS

WO 95/06025  3/1995  WIPO .

OTHER PUBLICATIONS

Miyakoshi, T. & S. Saito, "Addition of Alkyl Vinyl Ketone to Aldehydes Catalyzed by Tertiary Phosphine," *Nippon Kagaku Kaishi*, 11, 1623–1628 (1983).
Imagawa, T., et al., "Synthesis of 2–(1–Hydroxyalkyl) Acrylonitriles by the Cocatalysis of a Base and an Acid," *Synthetic Communications*, 14, 1267–1273 (1984).
Nagel, U., et al., "Synthesis of N–Substituted (R,R)–3,4–bis(diphenylphosphino) pyrrolidines. The Use of the Rhodium Complexes for the Asymmetric Hydrogenation of [α]–(Acylamino)acrylic Acid Derivatives," *Chem. Ber.*, 119, 3326–3343 (1986).
Drewes, S.E. & Roos, G., "Synthetic Potential of the Tetiary–Amine–Catalysed Reaction of Activated Vinyl Carbanions with Aldehydes," *Tetrahedron*, 44, 4653–4670 (1988).
Noyori, R. & Kitamura, M., "Enantioselective Catalysis with Metal Complexes. An Overview," *Modern Synthetic Methods*, 116–198 (1989).
Trost, B.M. & Fleming, I., "Transition Metal Mediated Cycloadditions," *Comprehensive Organic Synthesis*, Chapter 3.2, 271–314 (1991).

Jacobsen, E.N., "Asymmetric Catalytic Epoxidation of Unfunctionalized Olefins," *Catalytic Asymmetric Synthesis*, Chapter 4.2, 159–202 (1993).
Smith, M.B., "Retrosynthesis, Stereochemistry and Conformations," *Organic Synthesis*, Chapter 1.4.C, 58–63 (1994).
Trost, B.M. & Li, C–J, "Novel Umpolung in C—C Bond Formation Catalyzed by Triphenylphosphine," *J. AM. Chem. Soc.*, 116, 3167–3168 (1994).
Zhang, C. & Lu, X., "Phosphine–Catalyzed Cycloaddition of 2,3–Butadienoates or 2–Butynoates with Electron–Deficient Olefins. A Novel [3+2] Annulation Approach to Cyclopentenes," *J. Org. Chem.* 60, 2906–2908 (1995).
Aggarwal, V.K. et al., "A Novel Catalytic Cycle for the Synthesis of Epoxides Using Sulfure Ylides," *Chem. Eur. Journal*, 1024–1030 (1996).
Aggarwal, V.K., et al., "Direct Asymmetric Epoxidation of Aldehydes Using Catalytic Amounts of Enantiomerically Pure Sulfides," *J. Am. Chem. Soc.*, 118, 7004–7005 (1996).
Basavaiah, D, et al., "The Baylis–Hillman Reaction: A Novel Carbon–Carbon bond Forming Reaction," *Tetrahedron*, 52, 8001–8062 (1996).
Nozaki, K. et al., "Synthesis of Highly Functionalized y–Butyrolactones from Activated Carbonyl Compounds and Dimethyl Acetylenedicaarboxylate," *J. Org. Chem.*, 61, 4516–4519 (1996).
Li, A–H & Dai, L–X, "Asymmetric Ylide Reactions: Epoxidation, Cyclopropanation, Aziridination, Olefination, and Rearrangement," *Chem. Rev.*, 97, 2341–2372 (1997).
Birch, S. F. & Dean, R. A., "The Configurations of the Isomeric Forms of 1:3–Dimethylcyclopentane," *J. Chem. Soc.*, 2477–2481 (1953).
Greidinger, D. S. & Ginsburg, D., "Alicyclic Studies. XIII. Preparation and Reactions of 1,1'–Dicycloalkenyls," *Alicyclic Studies, XIII*, 22, 1406–1410 (1957).
Knowles, W.S., et al., "Catalytic Asymmetric Hydrogenation," *J.C.S. Chem. Comm.*, 10–11 (1972).
Kagan, H.B. & Dang, T., "Asymmetric Catalytic Reduction with Transition Metal Complexes. I. A Catalytic System of Rhodium (I) with (–)–2,3,O–Isopropylidene–2,3–dihydroxy–1,4–bis(diphenylphosphino)butane, a New Chiral Diphosphine," *J. Am. Chem. Soc.*, 94, 6429–6433 (1972).
Hajos, Z.G. & Parrish, D.R., "The Stereocontrolled Synthesis of trans–Hydrindan Steroidal Intermediates," *J. Org. Chem.*, 38, 3239–3243 (1973).
Kwart, H. & Conley, R.A. "Modified Birch Reductions. Lithium in n–Alkylamines," *J. Org. Chem.*, 38, 2011–2016 (1973).

(List continued on next page.)

*Primary Examiner*—Deborah C. Lambkin
*Attorney, Agent, or Firm*—Finnegan, Henderson, Farabow, Garrett & Dunner, LLP

[57] ABSTRACT

This invention relates to chiral heterocyclic compounds useful for asymmetric synthesis and catalysis. More particularly, the invention relates to chiral heterocyclic phosphine, sulfur, and nitrogen compounds for asymmetric synthesis and catalysis in the production of enantiomerically pure products.

20 Claims, No Drawings

OTHER PUBLICATIONS

Nagao, T., et al., "Studies on A New 1,5–Benzothiazepine Derivative (CRD–401). IV. Coronary Vasodilating Effect and Structure–Activity Relationship," *Chem. Pharm. Bull.*, 21, 92–97 (1973).

Sauer, G., et al., "Synthesis of D–Norgestrel," *Angew. Chem., Int. Ed.*, 14, 417 (1975).

Cohen, N., "Asymmetric Induction in 19–Norsteroid Total Synthesis," *Accounts of Chem. Research*, 9, 412–417 (1976).

Achiwa, K., "Asymmetric Hydrogenation with New Chiral Functionalized Bisphosphine–Rhodium Complexes," *J. Am. Chem. Soc.*, 98, 8265–8266 (1976).

Corey, E.J., et al., "New Reagents for the Intermolecular and Intramolecular Pinacolic Coupling of Ketones and Aldehydes," *J. Org. Chem.*, 41, 260–265 (1977).

Fryzuk, M.D. & Bosnich, B., "Asymmetric Synthesis. Production of Optically Active Amino Acids by Catalytic Hydrogenation," *J. Am. Chem. Soc.*, 99, 6262–6267 (1977).

Vineyard, B.D., et al., "Asymmetric Hydrogenation. Rhodium Chiral Bisphosphine Catalyst," *J. Am. Chem. Society*, 99, 5946–5952 (1977).

Whitesell, J.K. & Felman, S.W., "Asymmetric Induction. 2. Enantioselective Alkylation of Cyclohexanone via a Chiral Enamine," *J. Org. Chem.*, 42, 1663 (1977).

Kauffmann, T., "In Search of New Organometallic Reagents for Organic Synthesis," *Topics in Curr. Chem.*, 92, 111–147 (1980).

A. Miyashita, et al., "2,2'–Bis(Diphenylphosphino)–1,1'–Binaphthyl (BINAP), an Atropisomeric Chiral Bis(traryl)phosphino, and Its Use in the Rhodium(I)–Catalyzed Asymmetric Hydrogenation of α–(Acylamino)acrylic Acids," *J. Am. Chem. Soc.*, 102, 7932–7934 (1980).

Ojima, I. & Yoda, N., "N–Carbamoyl–4– Diphenylphosphino–2– Diphenylphosphinomethylphyrrolidines (CAPP). Efficient New Chiral Ligands for Asymmetric Hydrogenation," *Tetrahedron Lett.*, 21, 1051–1054 (1980).

Danheiser, R.L., et al. "(Trimethylsilyl) cyclopentene Annulation: A Regiocontrolled Approach to the Synthesis of Five–Membered Rings," *J. Am. Chem. Soc.*, 103, 1604–1606 (1981).

Harding, K.E. & Burks, S.R., "Synthesis of trans–2,5–Dimethylpyrrolidine by Intramolecular Amidomercuration," *J. Org. Chem.*, 46, 3920–3922 (1981).

MacNeil, P.A., et al., "Asymmetric Synthesis. Asymmetric Catalytic Hydrogenation Using Chiral Chelating Six–Membered Ring Disphosphines," *J. Am. Chem. Soc.*, 103, 2273–2280 (1981).

Brown, H.C., et al., "Hydroboration. 62. Monoisopinocampheylborane, an Excellent Chiral Hydroborating Agent for Trans–Disubstituted and Trisubstituted Alkenes. Evidence for a Strong Steric Dependence in Such Asymmetric Hydroborations," *J. Org. Chem.*, 47, 5074 (1982).

Wynberg, H. & Staring, E. G. J., "Asymmetric Synthesis of (S)–and (R)–Malic Acid from Ketene nad Chloral," *J. Am. Chem. Soc.*, 104, 166–168 (1982).

Danheiser, R.L., et al., "Scope and Stereochemical Course of the (Trimethylsilyl) Cyclopentene Annulation," *Tetrahedron*, 39, 935–947 (1983).

Wovkulich, P. M., et al., "Total Synthesis of 1α, 25(R)–Dihydroxy Vitamin $D_3$ 26,23(S)–Lactone (Calcitriol Lactone), a Natural Metabolite of Vitamin $D_3$," *J.Org. Chem.*, 48, 4433–4436 (1983).

Kozikowski, A. P. & Jung, S. H., "Phosphoniosilylation: An Efficient and Practical Method for the β–Functionalization of Enones," *J. Org. Chem.*, 51, 3400–3402 (1986).

Schlessinger, R. H., et al., "An Enantio–and Erythro–Selective Lithium Enolate Derived from a Vinylogous Urethan: Its Application as a $C_4$ Synthon to the Virginamycin $M_2$ Problem," *J. Org. Chem.*, No. 51, 3070–3073 (1986).

Takaya, H., et al,. "Practical Synthesis of (R)–or (S)–2, 2'–Bis (diarylphosphino)–1,1'–binaphthyls (BINAPs)," *J. Org. Chem.*, 51, 629–635 (1986).

Trost, B. M., "[3+2] Cycloaddition Approaches to Five–Membered Rings via Trimethylenemethane and Its Equivalents," *Angew. Chem. Int. Ed. Engl.*, 25, 1–20 (1986).

Binger, P. & Búch, H.M., "Cyclopropenes and Methylenecylopropanes as Multifunctional Reagents in Transition Metal Catalyzed Reactions," *Topics in Current Chemistry*, 135, 77–151 (1987).

Halterman, R.L., et al., "A Designed, Enantiomerically Pure, Fused Cyclopentadienyl Ligand with $C_2$ Symmetry: Synthesis and Use in Enantioselective Titanocene Catalyzed Hydrogenation of Alkenes," *J. Am. Chem. Soc.* 109, 8105–8106 (1987).

Schlessinger, R.H. & Iwanowicz, E.J., "The Synthesis of Either (+) or (–) Trans–2,5–Dimethylpyrrolidine," *Tetrahedron Lett.*, 28, 2083–2086 (1987).

Tomioka, K., et al., "Enantioface Differentiation in Cis Dihydroxylation of C—C Double Bonds by Osmium Tetroxide with Use of a Chiral Diamine with $D_2$ symmetry," *J. Am. Chem. Soc.*, 109, 6213–6215 (1987).

Brunner, H.,, "Enantioselective Synthesis with Optically Active Transition–Metal Catalysts," *Synthesis*, 645–654 (1988).

Feldman, K. S., et al., "Cyclopentane Synthesis via Free–Radical–Mediated Addition of Funtionalized Alkenes to Substituted Vinylcyclopropanes," *J. Am. Chem. Soc.*, 110, 3300–3302 (1988).

Goodridge, R.J., et al,. "Preparation of Stable, Camphor–Derived, Optically Active Allyl and Alkyl Sulfoxides and Thermal Epimerization of the Allyl Sulfoxides," *J. Org. Chem.*, 53, 2881–2889 (1988).

Padwa, A. & Yeske, P.E., "Synthesis of Cyclopentenyl Sulfones via the [3+2] Cyclization–Elimination Reaction of (Phenylsulfonyl)allene," *J. Am. Chem. Soc.*, 110, 1617–1618 (1988).

Schlessinger, R. H., et al., "Highly Diastereoselective Alkylation Reactions of Vinylogous Urethanes Derived from Simple Tetronic Acids," *Tetrahedron Lett.*, 29, 1489–1492 (1988).

Beak, P. & Burg, D. A.,. "An Anionic 3+2 Cyclization–Elimination Route to Cyclopentenes," *J. Org. Chem.*, 54, 1647–1654 (1989).

Consiglio, G & Waymouth, R.M., "Enantioselective Homogeneous Catalysis Involving Transition–Metal–Allyl Intermediates," *Chem. Rev.*, 89, 257–276 (1989).

Furukawa, N., et al., "Camphoryl Sulfides as a Chiral Auxillary and a Mediator for One–Step Synthesis of Optically Active 1,2–Diaryloxiranes," *J. Org. Chem.*, 54, 4222–4224 (1989).

Hudlicky T. & Price, J. D., "Anionic Approaches to the Construction of Cyclopentanoids," *Chem. Rev.*, 89, 1467–1468 (1989).

Porter, N. A., et al., "Regioselectivity and Diastereoselectively in Fre–Radical Macrocyclization," *J. Am. Chem. Soc.*, 111, 8309–8310 (1989).

Short, R. P., et al., "An Improved Synthesis of (−)−(2R, 5R)−2,5−Dimethylpyrrolidine," *J. Org. Chem.,* 54, 1755–1756 (1989).

Takahashi, H., et al., "Enantioselective Alkylation of Aldehyde Catalyzed by Disulfonamide–Ti(O–i–Pr)$_4$–Dialkyl Zinc System," *Tetrahedron Lett.,* 30, 7095–7098 (1989).

Whitesell, J. K., "C$_2$ SYmmetry and Asymmetric Induction," *Chem Rev.,* 89, 1581–1590 (1989).

Yamamoto, A., et al., "Asymmetric [3+2] Cycloaddition of 2−(Sulfonylmethyl)−2−Propenyl Carbonate Catalyzed by Chiral Errocenylphosphine–Palladium Complexes," *Tetrahedron Lett.,* 30, 375–378 (1989).

Burk, M.J., et al., "New Electron–Rich Chiral Phosphines for Asymmetric Catalysis," *Organometallics,* 9, 2653–55 (1990).

Chen,Z. & Halteman, R. L., "Asymmetric Synthesis of C$_2$–Symmetric Annulated Bicyclooctylcyclopentadienes," *Syn. Lett.,* 2, 103–105 (1990).

Juge, S., et al., "Efficient Asymmetric Synthesis of Optically Pure Tertieary Mono and Diphosphine Ligands," *Tetrahedron Lett.,* 31, 6357–6360 (1990).

Okada, Y., et al., "The First Synthesis of Chiral Phosphinocarboxylic Acid Ligands, Trans−2−(diphenylphosphino) Cycloalkanecarboxylic Acids. The Phosphine–Palladium Complexes Catalyzed Asymmetric Allylic Alkylation," *Tetrahedron Lett.,* 31, 3905–3908 (1990).

Stafford, J. A. & Heathcock, C. H., "Asymmetric Total Synthesis of (−)−Secodaphniphylline[1]," *J. Org. Chem.,* 55, 5433–5434 (1990).

Tanaka, K., et al., "The Cyclic Dipeptide cyclo[(S)–Phenylalanyl–(S)–histidyl] as a Catalyst for Asymmetric Addition of Hydrogen Cyanide to Aldehydes," *J. Org. Chem.,* 55, 181–185 (1990).

Tomioka, K. "Asymmetric Synthesis Utilizing External Chiral Ligands," *Synthesis,* 541–549 (1990).

Breau L. & Durst, T., "Preparation of Optically Active Epoxides Via Sulfur Ylides. Origin of the Chiral Induction," *Tetrahedron: Asymmetry,* 2, 367–370 (1991).

Burk, M.J., "C2–Symmetric Bis(phospholanes) and Their Use in Highly Enantioselective Hydrogenation Reactions," *J. Am. Chem. Soc.,* 113, 8518 (1991).

Chen, L. & Ghosez, L., "Intramolecular Cycloadditions of Keteniminium Salts. A Practical Asymmetric Synthesis of Prostaglandins," *Tetrahedron:Asymmetry,* 2, 1181–1184 (1991).

Chen, Z., et al,. "Assymmetric Synthesis and Metalation of C$_2$–Symmetric Annulated Bicyclootylcyclopentadienes," *Organometallics* 10, 3449–3458 (1991).

Defoin, A., et al., "Asymmetric Diels–Alder Cycloadditions with C$_2$–Symmetrical Chiral Carbamoylnitroso Dienophiles," *Helvetica Chimica Acta,* 74, 103–109 (1991).

Jacobsen, E. N., et al., "Highly Enantioselective Epoxidation Catalysts Derived from 1,2–Diaminocyclohexane," *J. Am. Chem. Soc.,* 113, 7063–7064 (1993).

Ohta, T. & Takaya, H., "Metal–catalyzed Cycloaddition of Small Ring Compounds," *Comprehensive Organic Synthesis,* 5, 1185–1205 (1991).

Porter, N. A., et al., "Acyclic Stereochemical Control in Free–Radical Reactions," *Acc. Chem. Res.,* 24, 296–304 (1991).

Porter, N., et al., "Steroselective Intermolecular Radical Additions to Amide–Substituted Alkenes," *J. Am. Chem. Soc.,* 113, 1791–1799 (1991).

Uozumi, Y. & Hayashi, T. "Catalytic Asymmetric Synthesis of Optically Active 2–Alkanols via Hydrosilylations of 1–Alkenes with a Chiral Monophosphine–Palladium Catalyst," *J. Am. Chem. Soc.,* 113, 9887–9888 (1991).

van der Steen, F.H. & van Koten, G., "Syntheses of 3–Amino–2–azetidinones: A Literature Survey," *Tetrahedron,* 47, 7503–7524 (1991).

Yamazaki, T., et al., "The Enantioselective Fluoracetamide Acetal Claisen Rearrangements of N–Fluoroacetyl–trans–(2R,5R)–2,5–Dimethylpyrrolidine," *Tetrahedron Lett.,* 32, 4267–4270 (1991).

Báckvall, J–E., et al., "Asymmetric Induction in [4+2] Cycloadditions of Chiral Enamines to 2–Phenylsulfonyl 1,3–Dienes," *Tetrahedron Lett.,* 33, 2417–2418 (1992).

Borthwick, A. D. & Biggadike, K., "Synthesis of Chiral Carbocyclic Nucleosides," *Tetrahedron,* 48, 571–623 (1992).

Chen, Z. & Halterman, R. L., "Enantioselective Catalytic Isomerication of an Unfunctionalized Achiral Alkene," *J. Am. Chem. Soc.,* 114, 2276–2277 (1992).

Huryn, D. & Okabe, M., "AIDS–Driven Nucleoside Chemistry," *Chem. Rev.,* 92, 1745–1768 (1992).

Miller, W. H., et al., "Phosphorylation of Carbovir Enantiomers by Cellular Enzymes Determines the Stereoselectivity of Antiviral Activity," *Journ. of Biol. Chem.,* 267, 21220–21224 (1992).

Roth, F., et al., "An Intramolecular Baylis–Hillman Reaction," *Tetrahedron Lett.,* 33, 1045–1048 (1992).

Snider, B. B. & Zhang, Q., "Asymmetric Induction in Manganese(III)–Based Oxidative Free–Radical Cyclizations of Chiral Esters and Amides," *Tetrahedron Lett.,* 33, 5921–5924 (1992).

Burk, M. J., et al., "Perparation and Use of C$_2$–Symmetric Bis(phospholanes): Production of α–Amino Acid Derivatives via Highly Enantioselective Hydrogenation Reactions," *J. Am. Chem. Soc.,* 115, 10125–10138 (1993).

Evans, D. A., et al., "Bis(oxazoline)–Copper Complexes as Chiral Catalysts for the Enantioselective Aziridination of Olefins," *J. Am. Chem. Soc.,* 115, 5328–5329 (1993).

Fuji, K., "Asymmetric Creation of Quaternary Carbon Centers," *Chem. Rev.,* 93, 2037–2066 (1993).

Ghera, E., et al., "Synthesis of Nitrocyclopentanes via a 3+2 Strategy," *J. Org. Chem.,* 58, 6716–6724 (1993).

Inanaga, J., et al., "Organic Synthesis with Trialkylphosphine Catalysts. Conjugate Addition of Alcohols to α,β–Unsaturated Alkynic Acid Esters," *Chemistry Letters,* 241–244 (1993).

Kim, M. & Lee, I. S., "Combined Chemical and Enzymatic Synthesis of (S,S)–2,5–Dimethylpyrrolidine," *Syn. Lett.,* 10, 767–768 (1993).

Li, Z., et al., "Asymmetric Alkene Aziridination with Readily Available Chiral Diimine–Based Catalysts," *J. Am. Chem. Soc.,* 115, 5326–5327 (1993).

Matsuki, K., et al., "Asymmetric Reduction of Aromatic Ketones. II. An Enantioselective Synthesis of Methyl(2R, 3S)–3–(4–Methoxyphenyl)glycidate," *Chem. Pharm. Bull.,* 41 643–648 (1993).

Nugent, W.A., et al., "Beyond Nature's Chiral Pool: Enantioselective Catalysts in Industry," *Science,* 259, 479–483 (1993).

Pearson A. J. & Zhu, P. Y., "Chiral Auxillary–Directed Asymmetric Nucleophile Additions to Arene–Manganese Tricarbonyl Complexes," *J. Am. Chem. Soc.,* 115, 10376–10377 (1993).

Burk, M. J., et al., "A Versatile Tandem Catalysis Procedure for the Preparation of Novel Amino Acids and Peptides," *J. Am. Chem. Soc.,* 116, 10847–10848 (1994).

Corey, E.J., et al., "First Example of a Highly Enantioselective Catalytic Diels–Alder Reaction of an Achiral $C_{2v}$-Symmetric Dienophile and an Achiral Diene," *J. Am. Chem. Soc.,* 116, 12089–12090 (1994).

Hayashi, T., et al., "Catalytic Asymmetric Reduction of Allylic Esters with Formic Acid Catalyzed by Palladium–MOP Complexes," *J. Am. Chem. Soc.,* 116, 775–776 (1994).

Hoppe, D., et al., "Enantioselective Synthesis via Sparteine–induced Asymmetric Deprotonation," *Pure & Appl. Chem.,* 66, 1479–1486 (1994).

Marinetti, A. & Richardm L., "Phospetanes as Chiral Ligands for Catalytic Asymmetric Reactions: Hydrosilylation of Olefins," *Organometallics,* 13, 3956–3962 (1994).

Trost, B.M. & Li, C., "Phosphine–Catalyzed Isomerization–Addition of Oxygen Nucleophiles to 2–Alkynoates," *J. Am. Chem. Soc.,* 116, 10819–10820 (1994).

Aggarwal, V.K., et al., "The Use of Chiral Sulfides in Catalytic Asymmetric Epoxidation," *Tetrahedron: Asymmetry,* 6, 2557–2564 (1995).

Andersson, P. G., et al., "Studies of Allylic Substitution Catalysed by a Palladium Complex of a $C_2$–Symmetric Bis(aziridine): Preparation and NMR Spectroscopic Investigation of a Chiral π–Allyl Species," *Chem. Eur. J.,* 1, 12–16 (1995).

Berrisford, D.J., "Catalytic Asymmetric C–C Bond Formation: New Enolato–and Organolithium Chemistry," *Angew. Chem. Int. Ed. Engl.,* 34, 178–180 (1995).

Bray, B. L., et al., "Improved Procedures for the Preparation of (+)–(aR,2S,4R)–4–Amino–2–Hydroxy–1–Hydroxymethyl Cyclopentane," *Tetrahedron Lett.,* 36, 4483–4486 (1995).

Hansen, K. B., et al., "Carbenoid Transfer to Imines; A New Asymmetric Catalytic Synthesis of Aziridines," *Angew. Chem. Int. Ed. Engl.* 34, 676–678 (1995).

Oishi, T., et al., "Asymmetric Baylis–Hillman Reactions Using Chiral 2,3–Disubstituted 1,4–Diazabicylo[2.2.2]octanes Catalysts under High–Pressure Conditions," *Tetrahedron: Asymmetry,* 6, 1241–1244 (1995).

McKinstry, L. & Livinghouse, T., "An Efficient Procedure for the Synthesis of C–Chiral Bisphosphines," *Tetrahedron,* 51, 7655–7666 (1995).

Solladié–Cavallo, A. & Diep–Vohuule, A., "A Two–Step Asymmetric Synthesis of (R)–Monoaryl Epoxides Using a Chiral Oxthaine as a Recoverable Reagent: Application to the Preparation of (R)–β–Adrenergic Compounds," *J. Org. Chem.,* 60, 3494–3498 (1995).

Trost, B. M., et al., "An Enantioselective Synthesis of cis–4–tert–Butoxycarbomoyl–1–methoxycarbonyl–2–cyclopentene –A Useful, General Building Block," *Chem.Eur.J.,* 1, 568–571 (1995).

Zhang, C. & Lu, X., "Umpolung Addition Reaction of nucleophiles to 2,3–Butadienoates Catalyzed by a Phosphine" *Syn. Lett.,* 645–646 (1995).

Aggarwal, A., et al., "Influence of Oxygen Ligation on [$Fe_4S_4$] Cluster Properties. Characterization of the Cys77Ser Mutant of *Chromatium vinosum* HiPIP," *J. Am. Chem. Soc.,* 118, 927–928 (1996).

Aggarwal, A., et al., "Novel Catalytic and Asymmetric Process for Aziridination Mediated by Sulfur Ylides," *J. Org. Chem.,* 61, 8368–8369 (1996).

Beak, P., et al., "Regioselective, Diastereoselective, and Enantioselective Lithiation–Substitution Sequences: ReactionPathways and Synthetic Applications," *Acc. Chem. Res.,* 29, 552–560 (1996).

Halterman, R. L., et al., "Synthesis, Structure Determination, and Reactivity of $C_2$–Symmetrical Ehtylene–Bridged ansa–Bis(DiMeBCOCp)titanium Dichlorides," *Organometallics,* 15, 3957–3967 (1996).

Hamada, Y., et al., "New Monodentate Chiral Phosphine 2,6–Dimethyl–9–phenyl–9–phosphabicyclo[3,3.1]nonane(9–PBN): Application to Asymmetric Allylic Substitution Reaction," *Tetrahedron Lett.,* 37, 7565–7568 (1996).

Lautens, M., et al., "Transition Metal–Mediated Cycloaddition Reactions," *Chem. Rev.,* 96, 49–92 (1996).

Li, A.H., et al., "Preparation of Enantiomerically Enriched (2R,3R)–or–(2S,3S)–trans–Diaryloxiranes via Camphor–Derived Sulfonium Ylides," *J. Org. Chem.,* 61, 489–493 (1996).

Martinez, L. E., et al., "Highly Efficient and Enantioselective Synthesis of Carbocyclic Nucleoside Analogs Using Selective Early Transition Metal Catalysis," *J. Org. Chem.,* 61, 7963–7966 (1996).

Solladié–Cavallo, A. & Diep–Vohuule, A., "A Two–step Asymmetric Synthesis of Pure Trans–(R,R)–Diaryl–epoxides," *Tetrahedron: Asymmetry,* 7, 1783–1788 (1996).

Trost, B.M. & Vranken, D.L., "Asymmetric Transition Metal–Catalyzed Allylic Alkylations," *Chem. Rev.,* 96, 395–422 (1996).

Trost, B.M., "Designing a Receptor for Molecular Recognition in a Catalytic Synthetic Reaction: Allylic Alkylation," *Acc. Chem. Res.,* 29, 355–364 (1996).

Tu, Y., et al., "An Efficient Asymmetric Epoxidation Method for trans–Olefins Mediated by a Fructose–Derived Ketone," *J. Am. Chem. Soc.,* 118, 9806–9807 (1996).

Vedejs, E., et al., "Enantioselective Acylations Catalyzed by Chiral Phosphines," *J. Org. Chem.,* 61, 430–431 (1996).

Yang, D., et al., "A $C_2$ Symmetric Chiral Ketone for Catalytic Asymmetric Epoxidation of Unfunctionalized Olefins," *J. Am. Chem. Soc.,* 118, 491–492 (1996).

Chen,Z., et al. "Syntheses of Novel Chiral Monophosphine, 2,5–Dialkyl–7–phenyl–7–phosphabicyclo–[2.2.1]heptanes, and Their Application in Highly Enantiioselective Pd–Catalyzed Allylic Alkylations," *J. Org. Chem.,* 62, 4521–4523 (1997).

Markó, I. E., et al., "Catalytic Enantioselective Baylis–Hillman Reactions. Correlation between Pressure and Enantiomeric Excess," *Tetrahedron ,* 53, 1015–1024 (1997).

Trost, B.M. & Dake, G.R., "Nucleophilic α–Addition to Alkynoates. A Synthesis of Dehydroamino Acids," *J. Am. Chem. Soc.,* 119, 7595–7596 (1997).

Xu, Z. & Lu, X., "Phosphine–Catalyzed [3+2] Cycloaddition Reaction of Methyl 2,3–butadienoate and N–Tosylimines. A Novel Approach to Nitrogen Heterocycles," *Tetrahedron Lett.,* 38, 3461–3464 1997).

ASYMMETRIC SYNTHESIS AND CATALYSIS WITH CHIRAL HETEROCYCLIC COMPOUNDS

This application claims the benefit of provisional application no. 60/035,187, filed Jan. 13, 1997 and provisional application No. 60/046,117, filed May 9, 1997.

FIELD OF THE INVENTION

This invention relates to chiral heterocyclic compounds useful for asymmetric synthesis and catalysis. More particularly, the invention relates to chiral heterocyclic phosphine, sulfur, and nitrogen compounds for asymmetric synthesis and catalysis in the production of enantiomerically pure products.

BACKGROUND OF THE INVENTION

The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects. A growing demand in pharmaceutical industries is to market a chiral drug in enantiomerically pure form.

To meet this challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is often the most efficient because a small amount of a chiral catalyst can be used to produce a large quantity of a chiral target molecule. During the last two decades, great effort has been devoted to discovering new asymmetric catalysts and more than a half-dozen commercial industrial processes have used asymmetric catalysis as the key step in the production of enantiomerically pure compounds.

The majority of current asymmetric catalytic processes relies on transition metal catalysts bearing chiral ligands. Asymmetric phosphine ligands have played a significant role in the development of transition metal catalyzed asymmetric reactions. While certain metal catalyzed phosphine chiral ligands have shown acceptable enantioselectivities in numerous reactions, there are a variety of reaction in which only modest enantioselectivity has been achieved with these ligands. The use of enzymes as asymmetric catalysts is limited because very few pure enzymes have been found to facilitate highly enantioselective catalytic reactions.

Given the limitations with transition metal catalysts and enzymes, the use of organic catalysts for asymmetric synthesis has attracted increasing attention. Compared with transition metal catalysts, there are several advantages of using pure organic catalysts: recovery of organic catalysts generally is easy since the catalysts are covalently bound and relatively stable; no contamination of toxic heavy metals exists during the reaction; and pure organic catalysts, as compared to metal catalysts, are environmentally benign.

Several organic asymmetric catalysts have been discovered and used in industrial applications. For example, chiral phosphines are known to catalyze a number of organic reactions. Vedejs et al., in the *Journal of Organic Chemistry* ("*J. Org. Chem.*"), Vol. 61, 8368 (1996), demonstrated phosphine-catalyzed enantioselective acylations of secondary alcohols. Whitesell and Felman, *J. Org. Chem.*, Vol. 42, 1663 (1977), used nitrogen-based chiral auxiliaries such as trans 2,5-dimethylpyrrolidine for organic synthesis.

This invention discloses several new chiral heterocyclic compounds for asymmetric synthesis and catalysis. These compounds contain rigid ring structures useful for restricting conformational flexibility of the compounds, thus enhancing chiral recognition. The invention provides chiral heterocyclic compounds which contain phosphorous, nitrogen, and sulfur atoms within the ring structure. The chiral heterocyclic compounds disclosed in the invention allow for new catalytic asymmetric processes, including reactions proceeding by a variety of methods described herein. In such a manner, the invention provides an efficient and economical method with which to synthesize chiral drugs and agrochemicals.

SUMMARY OF THE INVENTION

It is an object of the invention to provide chiral heterocyclic compounds for asymmetric synthesis and catalysis.

It is also an object of the invention to provide chiral heterocyclic phosphine, sulfur, and nitrogen compounds for asymmetric synthesis and catalysis in the production of enantiomerically pure products.

It is also an object of the invention to provide chiral heterocyclic phosphine, sulfur, and nitrogen compounds for asymmetric synthesis and catalysis in organic reactions such as [3+2] cycloaddition, nucleophilic gamma addition, Baylis-Hillman, acyl transfer, aziridation of aldehydes., epoxidation, thioether-mediation, alkylation, deprotonation, and other commonly known asymmetric carbon-carbon bond formations.

It is also an object of the invention to provide a method of making chiral heterocyclic phosphine, sulfur, and nitrogen compounds for asymmetric synthesis and catalysis.

It is also an object of the invention to provide an efficient and economical method with which to synthesize chiral drugs and agrochemicals.

In accordance with the invention, there is thus provided a chiral heterocyclic phosphine compound selected from each enantiomer of the formula I or II

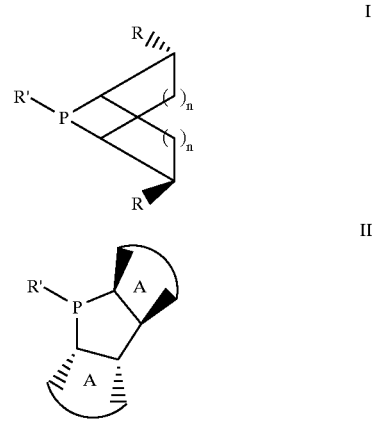

wherein n is 1 or 2; R is selected from alkyl having 1–8 carbon atoms, aryl, and substituted aryl; R' is selected from hydrogen, alkyl having 1–8 carbon atoms, aryl, and substituted aryl; and A is selected from a carbocyclic or heterocyclic, aromatic, saturated or partially saturated, mono-or bicyclic ring, which can be further substituted with one or more alkyl or aryl groups, and can comprise one or more additional chiral centers. In one embodiment of the invention, a chiral heterocyclic phosphine compound is provided as an asymmetric catalyst or a component of an asymmetric catalyst in organic reactions selected from [3+2] cycloaddition, nucleophilic gamma addition, Baylis-Hillman, acyl transfer, and other commonly known asymmetric carbon-carbon bond formations.

In accordance with another object of the invention, there is provided a chiral heterocyclic sulfur compound selected from each enantiomer of the formula III or IV

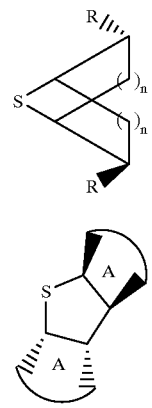

III

IV wherein n is 1 or 2; R is selected from alkyl having 1–8 carbon atoms, aryl, and substituted aryl, and A is selected from a carbocyclic or heterocyclic, aromatic, saturated or partially saturated, mono- or bicyclic ring, which can be further substituted with one or more alkyl or aryl groups, and can comprise one or more additional chiral centers. In one embodiment of the invention, a chiral heterocyclic sulfur compound is provided as an asymmetric catalyst or a component of an asymmetric catalyst in organic reactions selected from aziridation of aldehydes, epoxidation, thioether-mediation, and other commonly known asymmetric carbon-carbon bond formations.

In accordance with another object of the invention, there is provided a chiral heterocyclic nitrogen compound selected from each enantiomer of the formula V or VI

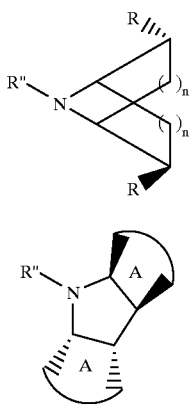

V

VI wherein n is 1 or 2; R is selected from alkyl having 1–8 carbon atoms, aryl, and substituted aryl; A is selected from a carbocyclic or heterocyclic, aromatic, saturated or partially saturated, mono- or bicyclic ring, which can be further substituted with one or more alkyl or aryl groups, and can comprise one or more additional chiral centers; R'' is selected from hydrogen, alkyl having 1–8 carbon atoms, aryl, substituted aryl, and a group of the formula VII or VIII

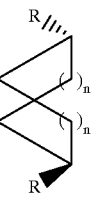

VII

VIII wherein the chiral nitrogen heterocycle in the group is identical to the other chiral nitrogen heterocycle in formula V or VI; and R''' is a diradical selected from alkyl diradicals having 1–8 carbon atoms, aryl diradicals, or substituted aryl diradicals. In one embodiment of the invention, a chiral heterocyclic nitrogen compound is provided as an asymmetric catalyst, a component of an asymmetric catalyst, or a chiral auxiliary in organic reactions selected from Baylis-Hillman, acyl transfer, alkylation, deprotonation, and other commonly known asymmetric carbon-carbon bond formations.

DETAILED DESCRIPTION OF THE INVENTION

This invention pertains to a chiral heterocyclic phosphine, sulfur, or nitrogen compound for asymmetric synthesis and catalysis in the production of enantiomerically pure products.

A suitable aryl of the invention includes phenyl, furan, thiophene, pyridine, pyrole, napthyl and similar aromatic rings. Substituted aryl refers to an aryl substituted with one or more alkyl groups having 1–8 carbon atoms, alkoxy having 1–8 carbon atoms, alkylcarbonyl having 1–8 carbon atoms, carboxy, alkoxycarbonyl having 2–8 carbon atoms, halo (Cl, Br, F or 1) amino, alkylamino or dialkylamino.

A suitable carbocyclic or heterocyclic, aromatic, saturated or partially saturated, mono- or bicyclic ring, which can be further substituted with one or more alkyl or aryl groups, and can comprise one or more additional chiral centers for use herein includes but is not limited to one derived from the parent compound furan, thiophene, pyrrole, tetrahydrofiran, tetrahydrothiopene, pyrrolidine, arsole or phosphole; or from the parent compound bipyridine, carbazole, benzofuran, indole, benzpyrazole, benzopyran, benzopyronone or benzodiazine.

Alkyls having 1–8 carbon atoms include straight or branched chain alkyls and cycloalkyls having 3 to 8 carbon atoms. Representative examples are methyl, ethyl, propyl, isopropyl, butyl, tertiary butyl, pentyl, cyclopentyl, hexyl cyclohexyl and the like. The alkyl group can be substituted with phenyl, substituted phenyl or alkoxy, carboxy, alkyoxycarbonyl, halo, amino, or alkyl amino or dialkylamino as defined above. Those skilled in the chemical art will recognize a wide variety of equivalent substituents.

A diradical is selected from alkyl diradicals having 1–8 carbon atoms, aryl diradicals, or substituted aryl diradicals.

A suitable diradical includes but is not limited to —CH$_2$CH$_2$—, —CH$_2$CH$_2$CH$_2$—, —CH$_2$CH$_2$CH$_2$CH$_2$—, —C$_6$H$_4$—, or ortho-substituted —C$_6$H$_4$—, and the like.

The invention encompasses a variety of asymmetric reactions utilizing catalysts of the invention, such as [3+2] cycloaddition, nucleophilic gamma addition, Baylis-Hillman, acyl transfer, aziridation of aldehydes, epoxidation, thioether-mediation, alkylation, deprotonation, and other commonly known asymmetric carbon-carbon bond formations. The catalyst of the invention provides efficient and practical methods for producing chiral drugs for antihypertensive, antihistamine, cardiovascular and central nervous system therapies. The chiral heterocyclic compounds of the invention are also important in the production of chiral agrochemicals.

CHIRAL, HETEROCYCLIC PHOSPHINE, SULFUR, AND NITROGEN COMPOUNDS

The invention provides chiral heterocyclic compounds containing phosphorous, sulfur, and nitrogen atoms. Chiral heterocyclic phosphine compounds, e.g., phosphabicyclo[2.2.1]heptanes I and phosphacycle II are shown in FIG. 1.

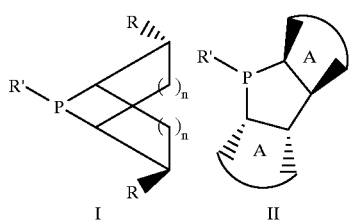

FIG.1

Both I and II contain rigid fused bicyclo structures which restrict conformational flexibility in the chiral system, leading to high enantioselectivity for a variety of asymmetric reactions described above.

The synthesis of chiral phosphabicyclo[2.2.1]heptanes depends on the availability of enantiomerically pure cyclic 1,4-diols (Scheme 1). Chen et al., *Organometallics*, Vol. 10, 3449 (1991) and Halterman et al. *Journal of the American Chemical, Society* ("*J. Am. Chem. Soc.*"), Vol. 109, 8105 (1987) have previously prepared chiral cyclopentadiene derivatives from chiral diols. Halterman has synthesized chiral diols 1 and 2 from the inexpensive starting materials p-xylene and p-diisopropylbenzene, respectivey.

The synthesis employed Birch reduction, followed by asymmetric hydroboration and recrystallization to 100% enantiomeric excess ("ee"). Conversion of the optically pure diols to Scheme I

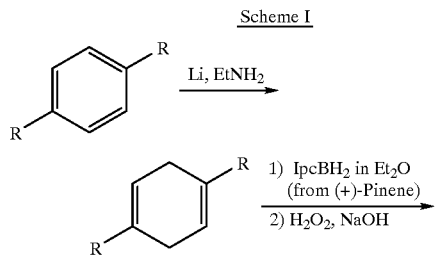

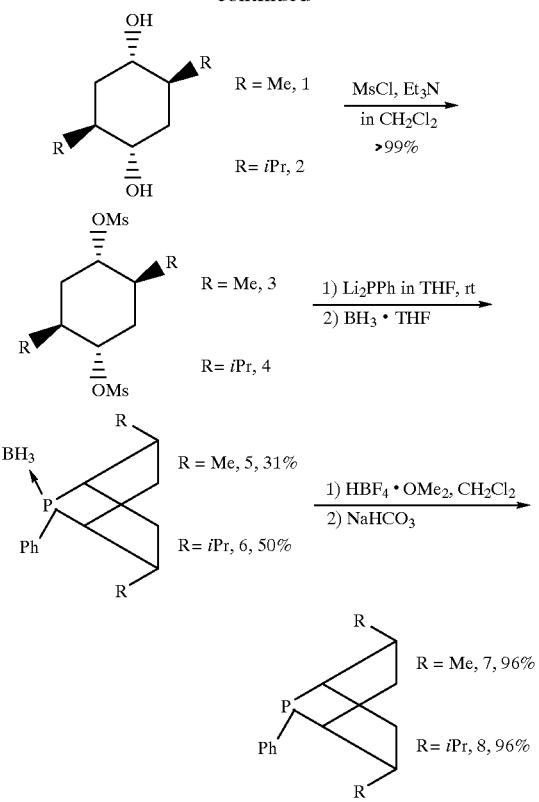

the corresponding mesylates proceeds cleanly. Nucleophilic substitution by Li$_2$PPh on the chiral dimesylates 3 and 4 generated the corresponding bicyclic phosphines, which were trapped by BH$_3$-THF to form the air-stable boron-protected monophosphines 5 and 6, respectively. Deprotection with a strong acid produces the desired products [7, (1R, 2S, 4R, 5S)-(+)-2,5-dimethyl-7-phenyl-7-phosphabicyclo[2.2.1]heptane; 8, (1R, 2R, 4R, 5R)-(+)-2,5-diisoprop-7-phenyl-7-phosphabicyclo-[2.2.1]heptane] in high yields.

The chiral phosphacycle 10 was synthesized by the route show in Scheme 2.

Scheme 2

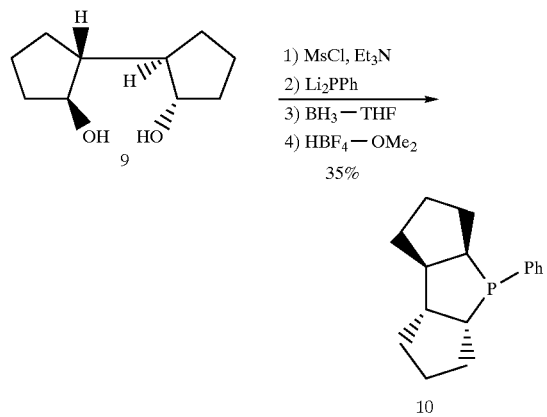

Chiral heterocyclic sulfur compounds, thiobicyclo[2.2.1]heptanes, III, and thiocycle IV, are shown in FIG. 2.

FIG. 2

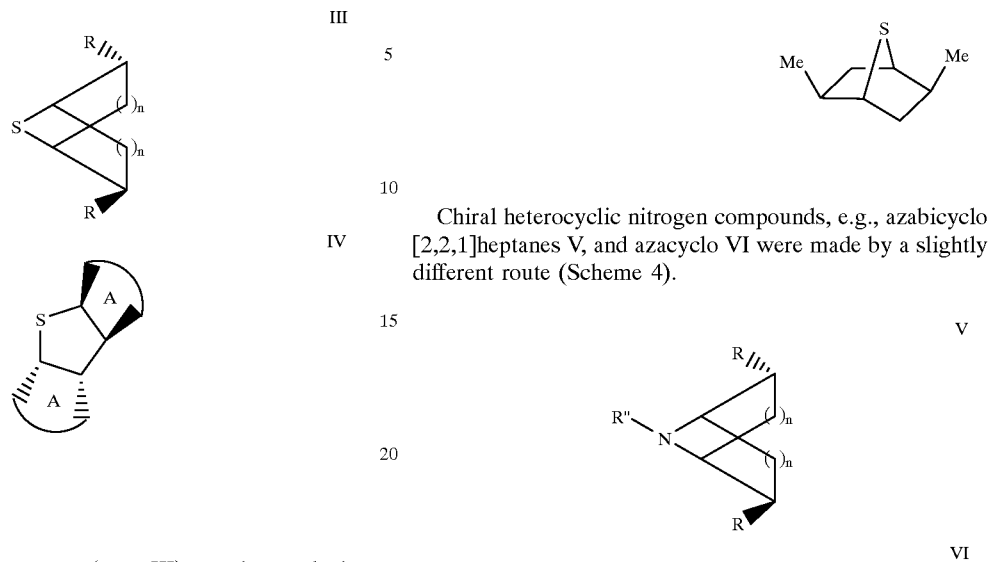

Thiobicyclo[2,2,1]heptanes (e.g., III) can be made by nucleophilic addition of $Na_2S$ to the chiral dimesylates (Scheme 3).

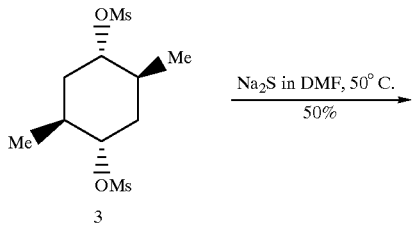

Scheme 3

Chiral heterocyclic nitrogen compounds, e.g., azabicyclo [2,2,1]heptanes V, and azacyclo VI were made by a slightly different route (Scheme 4).

Nucleophilic addition of azide to dimesylate 3 forms intermediate 12. Reduction of 12 with $H_2$ to an amine and intramolecular closure of the amine on to the mesylate occurs smoothly in the same operation gives the desired product 13. Further straightforward reactions lead to the other desired chiral nitrogen containing compounds 14 and 15.

Scheme 4

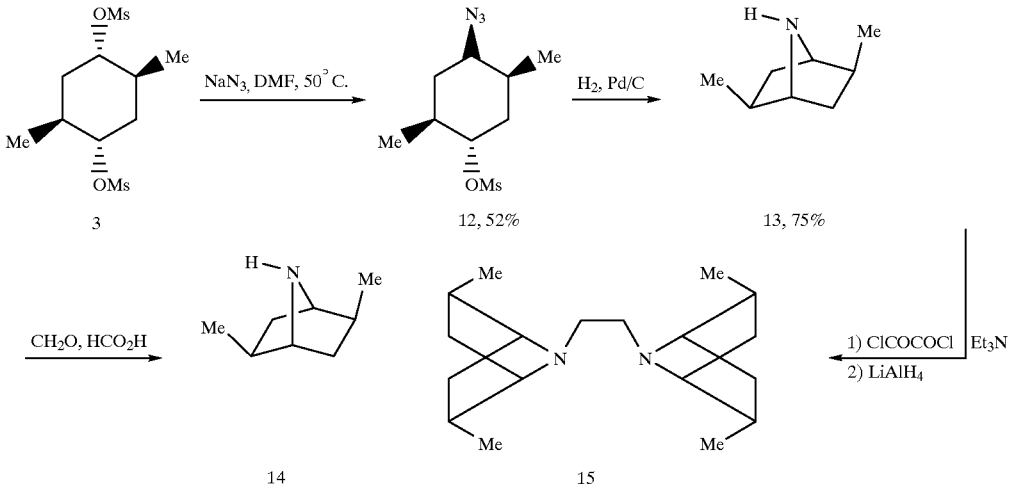

The sulfur and nitrogen chiral heterocyclic compounds of the general formula IV and VI were synthesized according to the method shown in Scheme 5.

Scheme 5

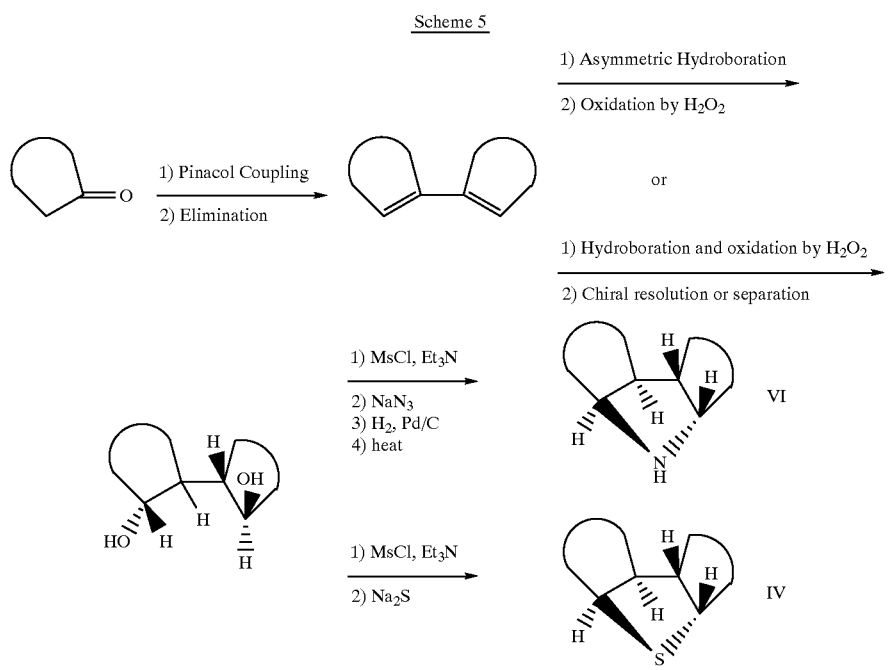

ASYMMETRIC SYNTHESIS AND CATALYSIS USING CHIRAL HETEROCYLIC COMPOUNDS

The invention is illustrated by using the chiral heterocyclic compounds of the invention in asymmetric synthesis and catalysis.

[3+2] CYCLOADDITIONS WITH CHIRAL HETEROCYCLIC COMPOUNDS

The identification of the prostaglandins, steroids and related natural products as important synthetic targets has stimulated the development of many diverse strategies for the synthesis of five-membered carbocycles. The efficient stereoselective synthesis of highly functionalized cyclopentane rings remains an important challenge in organic chemistry. Among the reported methods for the synthesis of five-membered ring carbocycles, [3+2] cycloadditions have the advantage of simultaneously forming multiple bonds, although issues of chemo-, regio-, diastereo- and enantioselectivity must be resolved if such a process is to achieve useful generality. Transition metal-catalyzed, anionic, cationic, and free radical mediated [3+2] cycloadditions have previously been investigated in the formation of five-member carbocycles. However, none of these methods produce the regioselectivity, enantioselectivity, and scope of application for the synthesis of cyclohexane derivatives.

Asymmetric [3+2] cycloadditions were conducted using several known chiral phosphine catalysts (16–18) to provide comparison points with [3+2] cycloadditions conducted with the chiral heterocyclic phosphine compound of the invention.

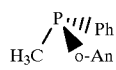

16

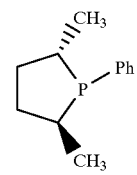

17

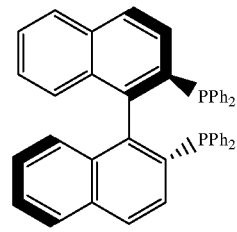

18

The asymmetric reactions were done by mixing ethyl 2,3-butadienoate and ethyl acrylate in benzene with 10 mol % of phosphine at room temperature. Table 1 lists the results with different chiral heterocyclic phosphine compounds.

TABLE 1

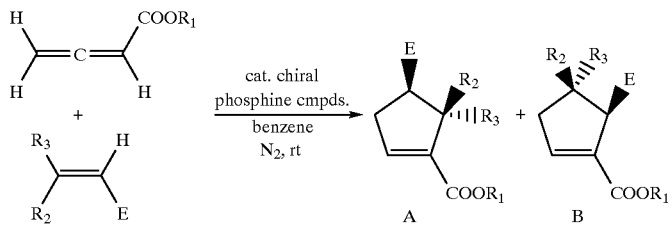

Phosphine-Catalyzed Asymmetric (3 + 2) Cycloaddition[a]

| Entry | Phospine | E | $R_1$ | $R_2$ | $R_3$ | solvent | T(°C) | Yield (%) | A:B[b] | % ee of A[b] | Config.[c] |
|---|---|---|---|---|---|---|---|---|---|---|---|
| 1  | 7  | COOEt            | Et  | H     | H     | benzene | rt | 66 | 95:5  | 81 | (−) R |
| 2  | 8  | COOEt            | Et  | H     | H     | benzene | rt | 76 | 97:3  | 81 | (−)R  |
| 3  | 16 | COOEt            | Et  | H     | H     | benzene | rt | 80 | 80:20 | 56 | (+)S  |
| 4  | 17 | COOEt            | Et  | H     | H     | benzene | rt | 83 | 79:29 | 6  | (+)S  |
| 5  | 18 | COOEt            | Et  | H     | H     | benzene | rt | 33 | 73:27 | 12 | (−)R  |
| 6  | 7  | COO$^{t Bu}$     | Et  | H     | H     | benzene | rt | 46 | 100:0 | 86 | (−)R  |
| 7  | 7  | COO$^{t Bu}$     | Et  | H     | H     | benzene | rt | 69 | 95:5  | 89 | (−)R  |
| 8  | 7  | COO$^{t Bu}$     | Et  | H     | H     | toluene | 0  | 42 | 97:3  | 93 | (−)R  |
| 9  | 8  | COOM             | Et  | H     | H     | benzene | rt | 87 | 96:4  | 79 | (−)R  |
| 10 | 8  | COO$^{t Bu}$     | Et  | H     | H     | benzene | rt | 92 | 100:0 | 88 | (−)R  |
| 11 | 8  | COO$^{t Bu}$     | Et  | H     | H     | toluene | 0  | 88 | 100:0 | 93 | (−)R  |
| 12 | 8  | COO$^{t Bu}$     | Et  | H     | H     | benzene | rt | 75 | 95:5  | 88 | (−)R  |
| 13 | 7  | COOEt            | tBu | H     | H     | benzene | rt | 13 | 97:3  | 89 | (−)R  |
| 14 | 8  | COOEt            | tBu | H     | H     | benzene | rt | 84 | 94:6  | 69 | (−)R  |
| 15 | 8  | COOEt            | Et  | COOEt | H     | benzene | rt | 49 | —     | 79 | (+)   |
| 16 | 8  | COOEt            | Et  | H     | COOEt | benzene | rt | 84 | —     | 36 | (−)   |

[a]The reaction was carried out under $N_2$ using a chiral phosphine (10 mol %), 2,3-butadienoate (100 mol %) and an electron deficient olefins (100 mol %).
[b]A:B and % ee were measured by GC using β and γ-DEX columns. The absolute configuration was determined by comparing the optical rotation with the literature value.

Phosphabicyclo[2.2.1]heptanes 7–8 are more effective both in terms of regioselectivity (A:B ratio) and enantioselectivity (% ee of A) than known chiral phosphines 16–18. The absolute configuration of product A was assigned by correlation with (1R, 3R)-dihydroxymethyl-3-cylopentane. In particular, the enantioselectivity with 7 (81% ee, R) is much higher than with 17 (6% ee, S), which illustrates the consequences of using a rigid bicyclic [2.2.1] structure rather than the conformationally more flexible five-membered ring phosphine.

Changing the size of ester group in the electron-deficient olefin alters the enantioselectivity. With phosphine 7, the enantioselectivity increases as the size of ester increases (entry 1, Et, 81% ee; entry 6, $^i$Bu, 86% ee; entry 7, $^t$Bu, 89% ee). A similar trend was observed with phosphine 8 (entries 2, 9–10, and 12). Upon cooling the reaction to 0° C. in toluene, up to 93% ee of A was obtained with phosphines 7–8 with excellent regioselectivity (entries 8 and 11). Increasing the size of the ester moiety in the 2,3-butadienoates, however, has different effects on the product ee with phosphine 7 (entry 1, Et, 81% ee; entry 13, $^t$Bu, 89% ee) or 8 (entry 2, Et, 81% ee; entry 14, $^t$Bu, 69% ee). A second major difference between catalysis by 7or 8 is in the yield of products. The conversion to the desired products with 8 is generally higher than with 7 (e.g., entries 6–8 vs entries 9–12). With diethyl maleate (entry 15) and diethyl fumarate (entry 16) as substrates, single cis- and trans-products were obtained with 8, respectively. While the % ee of the cis-product (entry 15, 79% ee) is slightly lower than the result with ethyl acrylate (entry 2, 81% ee), the trans-product has much lower optical purity (entry 16, 36% ee). As indicated by the Table 1, a [3+2] cycloaddition between 2,3-butadienoates and electron deficient olefins catalyzed by the chiral heterocyclic compounds of the invention provides cyclopentene products with excellent regioselectivity and enantioselectivity.

ASYMMETRIC NUCLEOPHILIC GAMMA ADDITION

The success of chiral heterocyclic phosphine catalyzed [3+2] cycloadditions between 2,3-butadienoates and electron-deficient olefins prompted further examination of other chiral heterocyclic phosphine catalyzed reactions. One such reaction, discovered by Trost, J. Am. Chem. Soc., Vol. 116, 3167 (1994), is the phosphine catalyzed "umpolung" C—C bond formation at the γ-position of 2-butynoates with malonate-type nucleophiles (Scheme 6). In this phosphine catalyzed "umpolung" C—C bond forming reaction, generation of electrophilic character at the γ-carbon of 2-butynoates creates a regiochemical complement to the Michael addition.

Using chiral phosphabicyclo[2.2.1]heptanes 7 and 8 as catalysts, and under conditions similar to those cited by Trost, moderate enantioselectivities (42–68% ee, entry 1–4) have been obtained between ethyl 2-butynoate and several pronucleophiles with 7 as the catalyst (Table 2).

Scheme 6

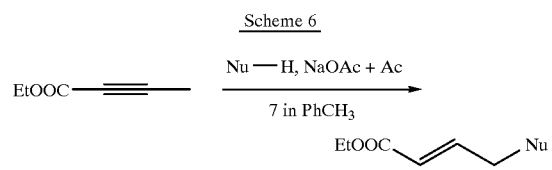

TABLE 2

Phosphine-Catalyzed Asymmetric γ-Addition[a]

| Entry | Substrate (NuH) | T (° C.) | Time (h) | Yield (%) | ee %[b] | Product |
|---|---|---|---|---|---|---|
| 1 | 2-methoxycarbonyl cyclopentanone | 80 | 16 | 76 | 59(−) | (19) |
| 2 | | 50 | 72 | 57 | 68(−) | |
| 3 | 3-ethoxycarbonyl tetrahydropyran-2-one | 110 | 50 | 44 | 51(+) | (20) |
| 4 | 3-acetyl γ-butyrolactone | 110 | 18 | 93 | 43(−) | (21) |

[a]: The reaction was carried out under $N_2$ with chiral phosphine 1 (30 mol %), NaOAc (50 mol %), acetic acid (50 mol %), ethyl 2-butynoate (100 mol %) and Nu-H (100 mol %).
[b]: % ee was measured by GC with a γ-Dex column.

Under milder reaction conditions, using ethyl 2,3-butadienoate as an electrophile instead of 2-butynoate, the γ-addition reaction was conducted under various conditions by changing ves, and substrates. Table 3 lists the results of this asymmetric reaction with phosphines (7,8, 10, 16–18).

TABLE 3

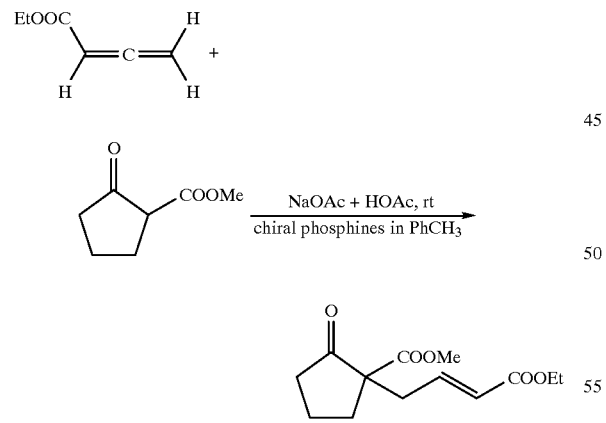

Asymmetric γ-Addition Catalyzed by Various Chiral Phosphines[a]

| Entry | Phosphine | Time | Yield (5) | ee %[b] | rotation |
|---|---|---|---|---|---|
| 1 | 7 | 27 h | 76 | 74 | — |
| 2 | 8 | 27 h | 80 | 69 | — |
| 3 | 10 | 18 | 71 | 35 | + |
| 4 | 16 | 4 d | 58 | 8 | — |
| 5 | 17 | 5 d | 66 | 20 | + |
| 6 | 18 | >10 d | 46 | 20 | + |

[a]: The reaction was carried out under $N_2$ at rt. With chiral phosphines (1–6) (10 mol %), NaOAc (50 mol %), AcOH (50 mol %), ethyl 2,3-butadienoate (100 mol %) and 2-methoxycarbonyl cyclopentanone (100 mol %).
[b]: % ee was measured by GC with a γ-Dex column.

The new phosphines 7 and 8 (entries 1–2) are more selective and active catalysts than the previously reported chiral phosphines 16–18 (entries 4–6). Compared to the conformationally rigid dimethyl phosphabicyclo[2.2.1]heptane 7 (entry 1, 74% ee), the corresponding five-membered ring phosphacycle 16 gives much lower enantioselectivity (entry 4, 8% ee). This result is similar to that observed in the asymmetric cyclic phosphine catalyzed [3+2] cycloaddition described above. Phosphacycle 10 produced moderate enantioselectivity (entry 3).

OTHER APPLICATIONS OF THE INVENTION

Many other asymmetric organic reactions can by facilitated by the chiral heterocyclic compounds of the invention. For example, the chiral heterocyclic nitrogen compound of general formula V or compound 15 can be used as chiral catalysts or auxiliaries for asymmetric deprotonation, enamine alkylation, cycloaddition reactions, and the Baylis-Hillman reaction. The dimer derivative of azabicyclo[2.2.1]heptane, 15, can serve as a chiral

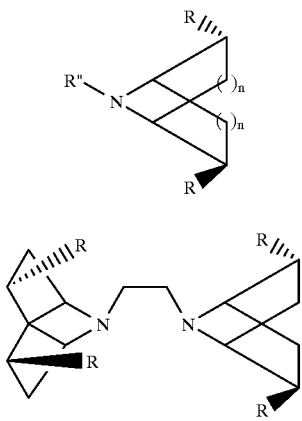

auxiliary in an asymmetric deprotonation. The fused [2.2.1] structure in V makes the nitrogen lone pair more nucleophilic than other trialkyl amines such as $Et_3N$.

The chiral heterocyclic sulfur compounds of the invention are particularly suited for use in asymmetric epoxidation of aldehydes. Most epoxidation systems are still not very efficient for unfunctionalized trans-olefins. Direct epoxidation of carbonyl compounds using sulfur ylides formed from III and IV provides a route for the formation of chiral trans epoxides. One target is (2R, 2S)-3-(4-methoxyphenyl) glycidate, which is a key intermediates for the synthesis of diltiazem hydrochloride, a potent blocker used for the treatment of anginina pectoris and hypertension.

Like epoxides, aziridines are important chiral building blocks in organic chemistry. Aggarwal et al., *J. Org. Chem.*, Vol. 61, 430 (1996), applied his epoxidation system for asymmetric aziridination by replacing aldehydes with imines as the substrates, with impressive selectivity results. The application of chiral heterocyclic sulfur compounds of the general formula III or IV as asymmetric catalysts should similarly provide high enantioselectivity for a variety of substrates.

EXAMPLES

Unless otherwise indicated, all reactions were carried out under nitrogen. THF and ether were freshly distilled from sodium benzophenone ketyl. Toluene and 1,4-dioxane were freshly distilled from sodium. Dichloromethane and hexane were freshly distilled from $CaH_2$. Column chromatography was performed using EM Silica gel 60 (230–400 mesh). $^1H$, $^{13}C$ and $^{31}P$ NMR were recorded at 300 or 360 MHZ NMR spectrometers. Chemical shifts are reported in ppm downfield from TMS with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis were done using chiral capillary columns (Supelco γ-Dex 225 or β-Dex 120).

Example 1

Compounds 1–4 (shown in Scheme 1) were prepared according to literature procedure. See, e.g., Halterman et al., Organometallic, Vol. 15, 3957 (1996); Halterman & Chen, *J. Am. Chem. Soc.*, Vol. 114, 2276 (1992).

Example 2

(1R, 2S, 4R, 5S)-(+)-2, 5-Dimethyl-7-phenyl-7-phosphabicyclo [2,2,1]heptane borane (5). To phenylphosphine (3.0 ml, 27.3 mmol) in THF (200 mL) was added n-BuLi (34.5 mL of a 1.6 M solution in hexane, 55 mmol) via syringe at −78° C. over 20 min. Then the orange solution was warmed up to rt and stirred for one hour at room temperature. To the resulting orange-yellow suspension was added a solution of (1S,2S,4S,5S)-2,5-dimethyl-cyclohexane-1,4-diol bis(methanesulfonate) (8.25 g, 27.5 mmol) in THF (100 mL) over 15 min. After the mixture was stirred overnight at room temperature, the pale-yellow suspension was hydrolyzed with $NH_4Cl$-saturated aqueous solution. The mixture was extracted with ether (2×50 mL), and the combined organic solution was dried over anhydrous sodium sulfate. After filtering, the solvents were removed under reduced pressure. The residue was taken into methylene chloride (100 mL) and treated with $BH_3THF$ (40 mL of a 1.0 M solution in THF, 40 mmol). After being stirred overnight, it was poured into $NH_4Cl$-saturated aqueous solution which was extracted with $CH_2Cl_2$ (3×50 mL). The combined organic solution was dried over anhydrous $Na_2SO_4$. After filtration, the solvent was removed on rotavapor. The residue was subjected to chromatography on silicon gel column, eluted with hexanes/$CH_2Cl_2$ (4:1). The product was isolated as a white solid, soluble in $CHCl_3$, THF, ether and AcOEt. Yield: 1.95 g (31%). $[\alpha]^{25}_D$=+59.5° (c 1.07, $CHCl_3$). $^1$H-NMR ($CDCl_3$): δ 7.60–7.30 (m, 5 H, $C_6H_5$), 2.60–2.40 (m, 2 H, CHP($BH_3$) Ph), 2.15–2.05 (m, 1 H, CH), 2.04–1.80 (m, 4 H, $CH_2$), 1.65–1.50 (m, 1 H, CH), 1.32 (d, $^3$J(HH)=6.5 Hz, 3 H, $CH_3$), 0.59 (d, $^3$J(HH)=6.7 Hz, 3 H, $CH_3$), 1.6–0.2 (br, $BH_3$); $^{13}$C-NMR ($CDCl_3$): δ 131.74 (d, $^2$J(PC)=7.3 Hz, $C_{ortho}$), 130.56 (d, $^1$J(PC)=43.9 Hz, $C_{ipso}$), 129.92 (d, $^4$J(PC)=2.0 Hz, $C_{para}$), 128.44 (d, $^3$J(PC)= 8.6 Hz, $C_{meta}$), 43.07 (d, $^1$J(PC)=30.5 Hz, CHP($BH_3$)Ph), 40.85 (d, $^1$J(PC)=31.6 Hz, CHP($BH_3$)Ph), 36.27 ($CH_2$), 36.67 (d, $^3$J(PC)=13.5 Hz, $CH_2$), 35.91 (d, $^2$J(PC)=3.5 Hz, CH), 34.65 (d, $^2$J(PC)=9.8 Hz, CH), 20.78 ($CH_3$) 20.53 ($CH_3$); $^{31}$P-NMR ($CDCl_3$): δ 36.3 (d, broad, $^1$J(PB)=58.8 Hz). MS m/z 232 ($M^+$, 0.42), 218 ($M^+$-$BH_3$, 100), 203 (7.41), 176 (14.60) 136 (9.81), 109 (16.67), 91 (6.59), 77 (5.51), 65 (3.71); HRMS Calcd for $C_{14}H_{22}BP$: 232.1552 ($M^+$); found: 232.1578; $C_{14}H_{19}P$: 218.1224 ($M^+$-$BH_3$); found: 218.1233.

Example 3

(1R, 2R, 4R, 5R)-(+)-2, 5-Diisopropyl-7-phenyl-7-phosphabicyclo[2,2,1]heptane borane (6). Using the same procedure as in the preparation of 5. Yield: 0.33 g (50%). $[\alpha]^{25}_D$=+25.5° (c 1.02, $CHCl_3$).$^1$H-NMR ($CDCl_3$): δ 7.55–7.30 (m, 5 H, $C_6H_5$), 2.85–2.70 9 (m, 2 H CHP($BH_3$) Ph), 2.30–2.20 (m, 1 H, CH), 2.18–2.00 (m, 1 H, CH), 1.95–1.65 (m, 4 H, $CH_2$), 1.40–1.20 (m, 2 H, CH), 1.03 (d, $^3$J(PH)=6.5 Hz, $CH_3$), 0.87 (d, $^3$J(PH)=6.7 Hz, $CH_3$), 0.85 (d, $^3$J(PH)=7.4 Hz, $CH_3$), 0.53 (s, broad, 3 H, $CH_3$), 1.5–0.2 (broad, $BH_3$); $^{13}$C-NMR ($CDCl_3$): δ C=131.19 (d, $^2$J(PC)= 8.3 Hz, $C_{ortho}$), 130.71 (d, $^1$J(PC)=45.2 Hz, $C_{ipso}$), 129.97 (d, $^4$J(PC)=2.5 Hz, $C_{para}$), 128.45 (d, $^3$J(PC)=9.5 Hz, $C_{meta}$), 50.30 (d, $^2$J(PC)=2.1 Hz, CH), 48.77 (d, $^2$J(PC)=9.7 Hz, CH), 38.27 (d, $^1$J(PC)=30.5 Hz, CHP($BH_3$)Ph), 36.81 ($CH_2$), 36.71 (d, $^1$J(PC)=31.5 Hz, CHP($BH_3$)Ph), 34.73 (d, $^3$J(PC)=13.7 Hz, $CH_2$), 31.92 ($CHMe_2$), 31.12 ($CHMe_2$), 22.41 ($CH_3$), 21.55 ($CH_3$), 20.73 ($CH_3$), 20.10 ($CH_3$); $^{31}$P-NMR ($CDCl_3$) δ 36.d (d, broad, $^1$J(PB)=51.4 Hz).

Example 4

(1R, 2S, 4R, 5S)-(+)-2, 5-Dimethyl-7-phenyl-7-phosphabicyclo[2,2,1]heptane (7) To a solution of corresponding borane complex of the phosphine (1.0 g, 4.31 mmol) in $CH_2Cl_2$ (22 mL) was added tetrafluoroboric acid-dimethyl ether complex (2.63 mL, 21.6 mmol) dropwise via a syringe at −5° C. After the addition, the reaction mixture was allowed to warm up slowly, and stirred at rt. After 20 h, $^{31}P$ NMR showed the reaction was over, it was diluted by $CH_2Cl_2$, neutralized by saturated $NaHCO_3$ aqueous solution. The aqueous layer was extracted with $CH_2Cl_2$. The combined organic solution was washed with brine, followed by water, and then dried over $Na_2SO_4$. Evaporation of the solvent gave a pure phosphine product, which was confirmed by NMR. Yield: 0.9 g (96%). $[\alpha]^{25}_D$=+92.5° (c 2.3, toluene); $^1H$ NMR (CDCl$_3$, 360 MHZ) α7.38~7.34 (m, 2H), 7.26~7.21 (m, 2H), 7.19~7.16 (m, 1H), 2.60~2.54 (m, 2H) 1.89~1.62 (m, 5H), 1.44~1.42 (m, 1H), 1.16 (d, J=6.12Hz, 3H), 0.55 (d, J=6.95 Hz, 3H); $^{13}C$ NMR (CDCl$_3$) δ 138.68 (d, J=29.3 Hz), 131.42 (d, J=13.0 Hz), 127.88 (d, J=2.35 Hz), 126.57 (s), 47.34 (d, J=13.5 Hz), 45.26 (d, J=10.2 Hz), 39.21 (d, J=6.7 Hz), 39.21 (d, J=5.3 Hz), 38.74 (d, J=6.7 Hz), 34.69 (d, 17.2 Hz), 22.37 (d, J=7.8 Hz), 21.52 (s); $^-$P NMR(CDCl$_3$) δ −7.29.

Example 5

(1R, 2R, 4R, 5R)-(+)-2, 5-Diisopropyl-7-phenyl-7-phosphabicyclo[2,2,1]heptane (8). Using the same procedure as in the preparation of 7. Yield: 1.0 g (95.5%). $[\alpha]^{25}_D$=+43.90° (c 1.2, toluene); $^1H$ NMR (CDCl$_3$, 360 MHZ) δ 67.35~7.30(m,2H),7.24~7.14 (m, 3H),2.94~2.85 (m, 2H), 1.76~1.53 (m, 5H), 1.25~1.14 (m, 2H), 1.06 (d, J=7.77Hz, 3H), 0.95~08.0 (m, 1H), 0.87 (dd, J=3.77 Hz, 7.89 Hz, 6 H), 0.49 (d, J=9.30 Hz, 3H); $^{13}C$ NMR (CDCl$_3$) δ 138.83 (d, J=30.49 Hz), 130.69 (d, J=12.2 Hz), 127.71 (d, J=2.87 Hz), 126.45 (s), 53.38 (d, J=6.34 Hz), 48.63 (d, J=17.06 Hz), 41.97 (d, J=13.43 Hz), 40.51 (d, J=9.96 Hz), 37.60 (d, J=11.09 Hz), 37.39 (d, J=9.74 Hz), 33.03 (d, 6.11 Hz), 31.86(s), 21.89 (s), 21.78 (s), 21.23 (s), 20.40 (s); $^{31}P$ NMR(CDCl$_3$) δ −7.49.

Example 6

Enantioselective [3+2] Cycloaddition: General Procedure for Asymmetric [3+21] Cycloaddition as Shown in Table 1. The procedure is exemplified by the reaction of ethyl 2,3-butadienoate and methyl acrylate in the presence of 8. Under the nitrogen, to a solution of ethyl 2,3-butadienoate (112 mg, 1.0 mmol) and methyl acrylate (0.9 ml, 10 mmol) in benzene (5 ml) was added chiral heterocyclic phospine compound 8 (1.0 ml of 0.1M solution in toluene, 0.1 mmol) dropwise via syringe at room temperature. After stirring the mixture for 3 hours, TLC showed the reaction was complete. The ratio of two regioisomers (A:B=96:4) and enantiomeric excesses of the crude reaction mixture (79% ee of A and 0% of B) were measured by Capillary GC. After the reaction mixture was concentrated in vacuo, the residue was purified by chromatography on a silica gel column (hexanes/ethyl acetate, 15:1). Yield: 175 mg, 87%.

Example 7

Preparation of Compound 10 (as shown in Scheme 2) (1R, 1'R)-Bicyclopentyl-(2S, 2'S)-diol Bis(methanesulfonate) (9). To a solution of (1R, 1'R)-bicycyclopentyl-(2S,2'S)-diol (0.8 g, 4.65 mmol) and triethylamine (1.68 mL, 12.09 mmol) in $CH_2Cl_2$ (30 mL) was added dropwise a solution of methanesulfonyl chloride (0.76 mL, 9.92 mmol) in $CH_2Cl_2$ (2 mL) at 0° C. After 30 min at 0° C., the reaction mixture was stirred for an 2 h at rt, then quenched by saturated aqueous ammonium chloride solution (25 mL).

The aqueous layer was extracted with $CH_2Cl_2$ (3+20 mL) and the combined organic solution was dried over $Na_2SO_4$. After evaporation of the solvent, a white solid was obtained which was used directly for the next step. $^1H$ NMR (CDCl$_3$, 200 MHZ) δ 6 5.01(m, 2H), 3.04 (s, 6 H), 2.17 (m, 2 H), 2.15–1.65 (m, 10 H), 1.43–1.52 (m, 2 H); $^{13}C$ NMR δ 86.8, 48.2, 38.4, 32.8, 27.4, 22.5.

10-BH$_3$. To phenylphosphine (0.39 mL, 3.55 mmol) in THF (50 mL) was added n-BuLi (4.9 mL of a 1.6 M solution in hexane, 7.8 mmol) via syringe at 0° C. over 2 min. The orange solution was warmed to rt and stirred for 1 h. To the resulting orange-yellow suspension was added a solution of (1R, 1'R)-bicyclopentyl-(2S, 2'S)-diol bis (methanesulfonate) (1.16 g, 3.55 mmol) in THF (30 mL) over 3 min. After the mixture was stirred overnight at rt, the pale-yellow suspension was hydrolyzed with saturated $NH_4Cl$ solution. The mixture was extracted with ether (2×50 mL), and the combined organic extract was dried over anhydrous $Na_2SO_4$, and evaporated. The residue was dissolved in $CH_2Cl_2$ (30 mL), treated with BH$_3$THF (10 mL of a 1.0 M solution in THF, 10 mmol) and the mixture was stirred overnight. Work up required addition of saturated $NH_4Cl$ solution and extraction with $CH_2Cl_2$ (30 mL). The combined organic extract was dried over anhydrous $Na_2SO_4$, and the solvent was removed under reduced pressure. The residue was subjected to silica gel chromatography, eluting with hexanes/$CH_2Cl_2$ (3:1) affording the product as a white solid. Yield: 0.35 g (38%). $^1H$-NMR (CDCl$_3$) δ 7.80–7.65 (m, 2 H), 7.55–7.35 (m, 3H), 3.00–2.10 (m, 4 H), 2.00–1.30 (m, 12 H), 1.30–0.20 (m, 3H); $^{13}C$-NMR CDCl$_3$) δ 132.2 (d, $^2J$(PC)=8.0 Hz), 130.8 (d, $^4J$(PC)=2.3 Hz), 129.3 (d, $^1J$(PC)=45.2 Hz), 128.6 (d, $^3J$(PC)=9.2 Hz), 53.5 (d, $^2J$(PC)=5.1 Hz), 52.6 (d, $^2J$(PC)=6.0 Hz), 45.3 (d, $^1J$(PC)=35.9 Hz), 41.0 (d, $^1J$(PC)=37.1 Hz), 32.3 (d, $^2J$(PC)=5.1 Hz), 32.0 (d, $^2J$(PC)=6.6 Hz), 28.1 (d, $^3J$(PC)=5.0 Hz), 27.8 (d, $^3J$(PC)=4.8 Hz), 26.1 (d, $^3J$(PC)=6.7 Hz), 25.8 (d, $^3J$(PC)=6.0 Hz); $^{31}P$-NMR (CDCl$_3$) δ 48.1 (q, br, $^1J$(PB)=53 Hz).

Preparation of Compound 10. To a solution of 10-BH$_3$ (0.293 g, 1.34 mmol) in $CH_2Cl_2$ (8 mL) was added tetrafluoroboric acid-dimethyl ether complex (0.69 mL, 5.69 mmol) dropwise via syringe at −5° C. After the addition, the reaction mixture was allowed to warm slowly to rt and was stirred for 20 h. When $^{31}P$ NMR showed the reaction was complete, the mixture was diluted with $CH_2Cl_2$, neutralized with saturated aqueous $NaHCO_3$ solution and the aqueous layer was extracted with $CH_2Cl_2$. The combined organic solution was washed with brine, followed by water, and then dried over $Na_2SO_4$. Evaporation of the solvent gave a pure phosphine product 10. Yield: 0.256 g (92%). $^1H$ NMR (CDCl$_3$, 360 MHZ) δ 7.46~7.42 (m, 2H), 7.35~7.26 (m, 3H), 2.93–2.77 (m, 2 H), 2.50–2.40 (m, 2 H), 2.09–2.01 (m, 1H), 1.87–1.42 (m, 10) 1.28–1.9 (m, 1 H); $^3C$ NMR (CDCl$_3$) δ 139.46 (s), 139.20 (s), 132.28 (s), 132.09 (s), 127.91 (d, J=5.25 Hz), 127.42 (s), 54.48 (d, J=1.99 Hz), 53.34 (s), 44.85 (d, J=13.40 Hz), 44.13 (d, J=6.61 Hz), 32.49 (m), 32.23 (s), 31.89 (s), 29.09 (d, J=5.16Hz) 26.05 (s), 25.60 (d, J=7.88 Hz); $^{31}P$ NMR (CDCl$_3$) δ 16.33.

I claim:

1. A chiral heterocyclic phosphine compound selected from each enantiomer of the formula I or II

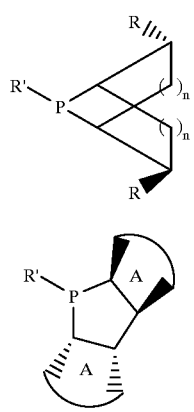

wherein:
  n is 1 or 2;
  R is selected from alkyl having 1–8 carbon atoms, aryl, and substituted aryl;
  R' is selected from hydrogen, alkyl having 1–8 carbon atoms, aryl, and substituted aryl; and
  A is selected from a carbocyclic or heterocyclic, aromatic, saturated or partially saturated, mono- or bicyclic ring, which can be further substituted with one or more alkyl or aryl groups, and can comprise one or more additional chiral centers.

2. A compound according to claim 1, wherein R is methyl, ethyl, or isopropyl.

3. A compound according to claim 2, wherein R' is phenyl.

4. A compound according to claim 1 wherein the ring comprises 3 to 8 carbon or heteroatoms per ring.

5. A compound according to claim 4 selected from each enantiomer of

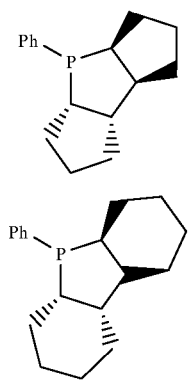

-continued

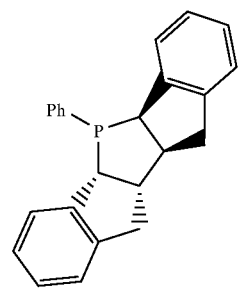

wherein Ph is phenyl.

6. A chiral heterocyclic phosphine compound according to claim 1 used as an asymmetric catalyst or as a component of an asymmetric catalyst in organic reactions selected from [3+2] cycloaddition, nucleophilic gamma addition, Baylis-Hillman, acyl transfer, and other commonly known asymmetric carbon-carbon bond formations.

7. A chiral heterocyclic sulfur compound selected from each enantiomer of the formula III or IV

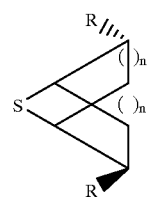

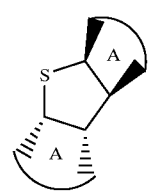

wherein:
  n is 1 or 2;
  R is selected from alkyl having 1–8 carbon atoms, aryl, and substituted aryl; and
  A is selected from a carbocyclic or heterocyclic, aromatic, saturated or partially saturated, mono- or bicyclic ring, which can be further substituted with one or more alkyl or aryl groups, and can comprise one or more additional chiral centers.

8. A compound according to claim 7, wherein R is methyl, ethyl, or isopropyl.

9. A compound according to claim 7, wherein the ring comprises 3 to 8 carbon or heteroatoms per ring.

10. A compound according to claim 9 selected from each enantiomer of

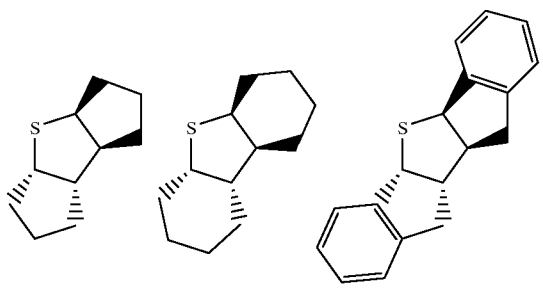

11. A process for asymmetric carbon-carbon bond formation, comprising carrying out said asymmetric carbon-carbon bond formation in the presence of a chiral heterocyclic sulfur compound according to claim 7.

12. A chiral heterocyclic nitrogen compound selected from each enantiomer of the formula V or VI

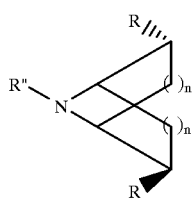

V

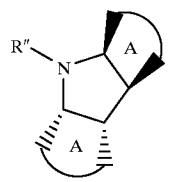

VI wherein:
  n is 1 or 2;
  R is selected from alkyl having 1–8 carbon atoms, aryl, and substituted aryl;
  A is selected from a carbocyclic or heterocyclic, aromatic, saturated or partially saturated, mono- or bicyclic ring, which can be further substituted with one or more alkyl or aryl groups, and can comprise one or more additional chiral centers;
  R" is selected from hydrogen, alkyl having 1–8 carbon atoms, aryl, substituted aryl, and a group selected from each enantiomer of the formula VII or VIII

VII

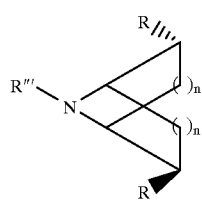

VIII

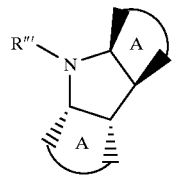

wherein
  the chiral nitrogen heterocycle in the group is identical to the other chiral nitrogen heterocycle in formula V or VI; and
  R'" is a diradical selected from alkyl diradicals having 1–8 carbon atoms, aryl diradicals, or substituted aryl diradicals.

13. A compound according to claim 12, wherein R is methyl, ethyl, or isopropyl.

14. A compound according to claim 13, wherein R" is methyl.

15. A compound according to claim 12 wherein the ring comprises 3 to 8 carbon or heteroatoms per ring.

16. A compound according to claim 12 wherein the diradical is —$CH_2CH_2$—, —$CH_2CH_2CH_2$—, —$CH_2CH_2CH_2CH_2$—, —$C_6H_4$—, or ortho-substituted-$C_6H_4$—.

17. A compound according to claim 12 selected from eaach enantiomer of

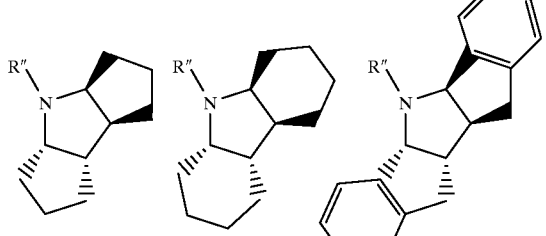

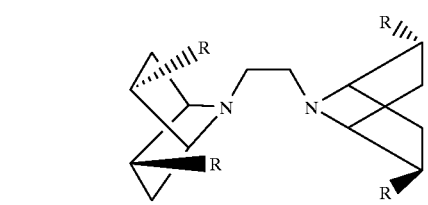

18. A process for asymmetric carbon-carbon bond formation, comprising carrying out said asymmetric carbon-carbon bond formation in the presence of a chiral heterocyclic nitrogen compound according to claim 12.

19. A process according to claim 11, wherein said asymmetric carbon-carbon bond formation occurs as part of an organic reaction selected from aziridation of aldehydes, epoxidation, and thioether-mediation.

20. A process according to claim 18, wherein said asymmetric carbon-carbon bond formation occurs as part of an organic reaction selected from a Baylis-Hillman reaction, acyl transfer, alkylation, and a deprotonation reaction.

* * * * *